(12) United States Patent
Lu

(10) Patent No.: US 7,238,338 B1
(45) Date of Patent: Jul. 3, 2007

(54) SYSTEM AND METHOD FOR THE LARGE SCALE LABELING OF COMPOUNDS WITH RADIOHALOGENS

(75) Inventor: Jianming Lu, Delta (CA)

(73) Assignee: Triumf, Vancouver, BC (CA)

( * ) Notice: Subject to any disclaimer, the term of this patent is extended or adjusted under 35 U.S.C. 154(b) by 359 days.

(21) Appl. No.: 10/174,960

(22) Filed: Jun. 20, 2002

Related U.S. Application Data

(60) Provisional application No. 60/299,762, filed on Jun. 22, 2001.

(51) Int. Cl.
| | |
|---|---|
| A61K 51/00 | (2006.01) |
| C07H 1/00 | (2006.01) |
| C12P 19/30 | (2006.01) |
| C12P 19/38 | (2006.01) |

(52) U.S. Cl. .................. 424/1.11; 424/1.65; 424/1.73; 435/87; 435/89; 536/1.11

(58) Field of Classification Search ................ 424/1.73, 424/1.11, 1.65; 536/1.11
See application file for complete search history.

(56) References Cited

U.S. PATENT DOCUMENTS

| | | | |
|---|---|---|---|
| 55,563 | A | 12/1866 | Webb et al. |
| 4,321,208 | A | 3/1982 | Sahadevan |
| 4,851,520 | A | 7/1989 | Kassis et al. |
| 4,880,615 | A | 11/1989 | Charleson |
| 5,077,034 | A | 12/1991 | Kassis et al. |
| 5,384,113 | A | 1/1995 | Deutsch et al. |
| 5,468,853 | A | 11/1995 | Baranowska-Kortylewicz |
| 5,574,148 | A | 11/1996 | Kassis et al. |
| 5,679,318 | A | 10/1997 | Vanderheyden et al. |
| 5,720,935 | A | 2/1998 | Kassis et al. |
| 5,811,073 | A | 9/1998 | Kassis et al. |
| 5,961,955 | A | 10/1999 | Shochat et al. |
| 6,066,309 | A | 5/2000 | Zamora et al. |
| 6,338,835 | B1 | 1/2002 | Shochat et al. |
| 2001/0055563 | A1 | 12/2001 | Zamora et al. |

FOREIGN PATENT DOCUMENTS

| | | |
|---|---|---|
| DE | 4237430 C1 | 3/1994 |
| WO | WO 97/28181 | 8/1997 |
| WO | WO 98/55154 | 12/1998 |
| WO | WO 99/62546 | 12/1999 |
| WO | WO 01/03745 A2 | 1/2001 |

OTHER PUBLICATIONS

McDevitt, Michael R. et al. "Preparation of α-Emitting $^{213}$Bi-Labeled Antibody Constructs for Clinical Use." *The Journal of Nuclear Medicine* vol. 40. No. 10 (Oct. 1997) pp. 1722-1727.
Zalutsky, Michael R. et al. "High-Level Production of α-Particle-Emitting$^{211}$ At and Preparation of$^{211}$ At-Labeled Antibodies for Clinical Use." *The Journal of Nuclear Medicine* vol. 42 No. 10 (Oct. 2001) pp. 1508-1515.
XP-001118543; "Vitamins as Radioprotectors In Vivo. I. Protection by Vitamin C Against Internal Radionuclides in Mouse Testes: Implications to the Mechanism of Damage Caused by the Auger Effect"; Radiation Research, Academic Press Inc.; vol. 137, No. 3 (Jan. 1997); pp. 394-399.
XP-002234773; "Enzymic Radioiodination of Polypeptide Hormones and Their Stability During Storage".
Culbert, et al., *Appl. Radiat. Isot.*, vol. 48, No. 6, pp. 745-747, 1997.
Adam et al., *Journal of Labelled Compounds and Radiopharmaceuticals*, vol. 31, No. 1, pp. 4-10, 1991.

*Primary Examiner*—Christina Chan
*Assistant Examiner*—Phuong Huynh
(74) *Attorney, Agent, or Firm*—Harness, Dickey & Harness

(57) ABSTRACT

Disclosed are methods for manufacturing radiohalogen-labeled steroids, nucleosides, nucleotides and proteins, for example, pyrimidines and proteins. Methods according to the example embodiments specific to pyrimidines includes dissolving a halogenated pyrimidine to obtain an initial solution, adding bis(tributyltin) and triphenylphosphine palladium to produce a catalyzed solution, heating the catalyzed solution under conditions sufficient to induce a reaction that produces an intermediate solution including a stannylated pyrimidine compound, removing substantially all of the first solvent from the intermediate solution to obtain an intermediate composition, purifying the resulting solution to obtain a purified composition including a stannylated pyrimidine, reacting the stannylated pyrimidine compound with a radiohalogen in a buffered reaction mixture to produce the radiohalogenated pyrimidine, adding an antioxidant and extracting the radiohalogenated pyrimidine from the reaction mixture. The extracted radiohalogenated pyrimidine(s) may be utilized in forming diagnostic and/or therapeutic products.

23 Claims, 1 Drawing Sheet

SYSTEM AND METHOD FOR THE LARGE SCALE LABELING OF COMPOUNDS WITH RADIOHALOGENS

RELATED APPLICATIONS

The present application claims priority under 35 U.S.C § 119 of U.S. Provisional Application 60/299,762, filed Jun. 22, 2001.

FIELD OF THE INVENTION

The present invention is generally related to a large scale method for making radio-halogenated compounds, preferably radio-labeled nucleotides and nucleosides ("radionucleotides", "radionucleosides"), steroids, or proteins such as antibodies. The invention resides in part in the finding that addition of an antioxidant, preferably ethanol or vitamin C (ascorbic acid), or a mixture of both, to the radiolabeled compound during its preparation and/or storage, allows retention of biological or chemical activity of the radiolabeled compound. One embodiment of the invention is a novel technique for large-scale production of deoxyuridines labeled with radioisotopes of halogens ("radiohalogens").

BACKGROUND OF THE INVENTION

Many diagnostic medical procedures require radiation sources that are introduced into a tissue or ingested by the patient. Such radiation sources preferably have a lifetime of a few hours—enough time to complete the diagnosis, but short enough that damage to tissue from the radiation is avoided and the radioisotope does not decay. Such radiation sources are preferably not chemically poisonous 5'-radiohalogenated-2'-deoxyuridine labeled with radioactive isotopes is such a radiation source. Specifically, iododeoxyuridine labeled with radioisotopes of iodine ("radioiodine") is such a radiation source.

The lifetime of radioactive isotopes of halogens varies from minutes to days. Radiohalogens are not chemically poisonous in tracer quantities. Radioactive isotopes of halogens have therefore found many uses in making medical and radiopharmaceutical products. One such product is iododeoxyuridine labeled with radioisotopes of iodine. One potential important use is the treatment of neoplastic meningitis with methotrexate and 5-[$^{125}$I]iodo-2'-deoxyuridine (125IudR). Iododeoxyuridine labeled with radioisotopes of iodine may also prove to be significant therapy for cancer. See, e.g., U.S. Pat. No. 5,077,034, hereby incorporated by reference. Additional uses may include treatment of colorectal tumors, lung tumors and arteriolosclerosis.

Radiohalogenated steroids and proteins can be used to image binding sites for these molecules in a subject or in in vitro assays of binding of such ligands to their receptors.

Several methods are used to label compounds with radiohalogens. These methods are limited by the amount of product they produce and the chemical purity and stability of the compound produced. An additional limitation is the time required to produce the compound must be compatible with the short life of some radioisotopes.

Technical and economic considerations are critical factors in choosing a method for the production of radio-halogenated compounds. Accordingly, a better, more efficient and less costly method of producing radio-halogenated compounds, such as steroids, proteins or nucleotides and nucleosides, for example, iododeoxyuridine labeled with radioisotopes of iodine is needed.

The present invention for large-scale production is simplified, rapid, produces higher yields, can be scaled up and provides an increase in stability of the radio-labeled compound. Typical procedures produce quantities of the scale 50 to 500 micro Ci. This novel method can produce batches of 100 milli Ci to 1 Ci in less time than the methods of the prior art. Specific activities of 1000 to 3000 Ci/mmol can be achieved in the product for labeled nucleoside, nucleotide or derivatives thereof or for labeled steroid products. Specific activities of from 10 to 40 mCi/nanogram can be achieved for labeled protein or labeled peptide products.

BRIEF DESCRIPTION OF THE DRAWING

Other aspects and advantages of the present invention will become apparent, upon reading the detailed description and accompanying drawing given herein below, which is given by way of illustration only, and which is not limitative of the present invention, wherein.

DETAILED DESCRIPTION OF THE INVENTION

Figure 1:
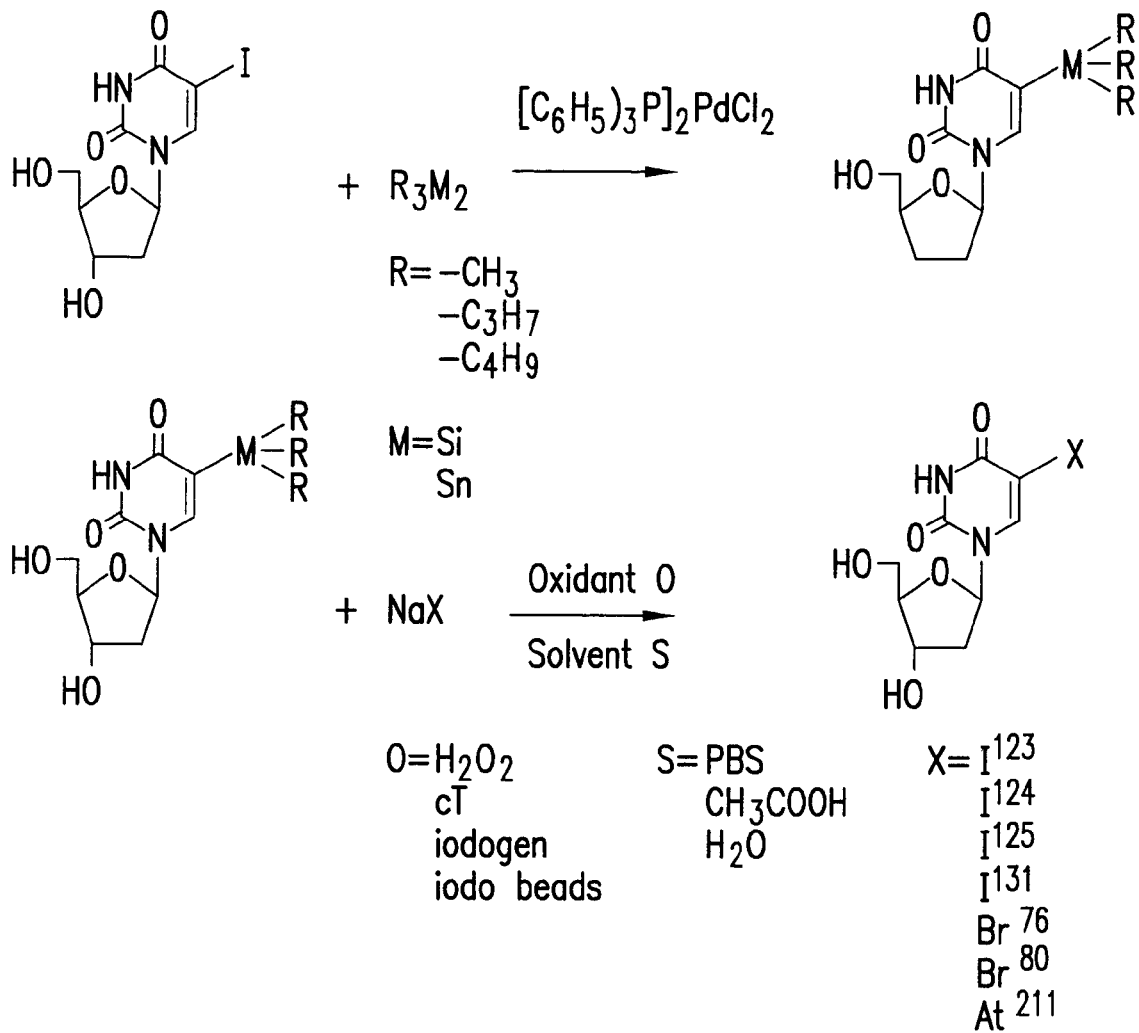
FIG. 1 shows the synthesis of labeled iododeoxyuridine.

The invention presents a method for preparing radiohalogen labeled compounds. The radiohalogen is can be a radioisotope of any halogen, such as a radioactive isotope of fluorine or bromine, but is preferably a radioiodine selected from $^{125}$I, $^{123}$I and $^{132}$I. The compounds to be prepared can be labeled nucleosides, nucleotides, or derivatives thereof, or can be steroids, or proteins or peptides. Preferred steroids are estradiol, progesterone and 17 (OH) progesterone. Preferred proteins are antibodies, such anti-TSH antibody. In a preferred embodiment of the invention, radiolabeled nucleotides or nucleosides, such as deoxypyrimidine, particularly deoxyuridine, are labeled with radioisotopes of halogens. The method of the invention accomplishes the synthesis of the radiolabeled compound using less time and in larger quantities. Due to less radiologic damage, the resulting product is more stable with respect to biological and/or chemical activity than the products obtained in the prior art.

The present invention constitutes an improvement over prior art methods for producing radiolabeled steroids, antibodies, and nucleosides, nucleotides and derivatives thereof. Pyrimidine nucleoside or nucleotides, e.g. uridine, thymine or cytosine, and derivatives thereof, are preferred nucleotides and nucleosides to be used in the invention. The invention can be applied to the synthesis of any labeled pyrimidine nucleosides or derivatives such as ribonucleosides, deoxyribonucleosides and 2',3' dideoxynucleosides and 5' sugar-derivatized nucleosides such as 5'-galactosyl derivatives and similarly to corresponding mono-, di- and triphosphonucleotides.

The invention can also be applied to the production of radiohalogen labeled steroids and proteins. Being commonly used in imaging or therapeutic protocols, antibodies are a preferred embodiment of a protein to be used in the present invention.

Briefly, the invention resides in the discovery that addition of an antioxidant to the labeling reaction solution after the labeling reaction has proceeded, with maintenance of the presence of the antioxidant during separation and packaging, results in production of a labeled product having higher biological activity of the pyrimidine nucleoside or nucleotide or derivative thereof.

In a preferred embodiment a pyrimidine nucleoside, for example, iododeoxyuridine, is labeled with a radioisotope of iodine.

The synthesis of halogenated pyrimidine nucleosides is known in the art. Exemplary syntheses are described by Kassis et al. in U.S. Pat. Nos. 5,720,935, 4,851,520 and PCT publication WO 01/05439, each of which is hereby incorporated by reference in its entirety and for all purposes. Another synthesis is described by Baranowska-Kortylewicz et al., U.S. Pat. No. 5,468,853, hereby incorporated by reference in its entirety and for all purposes. Baranowska-Kortylewicz et al. also describe the synthesis of 5' sugar derivatized pyrimidine nucleosides and their use in treatment of cancers; see WO 01/03745, hereby incorporated by reference in its entirety and for all purposes.

Similarly, methods for radioactive labeling of steroid compounds and proteins with a radiohalogen, including radioiodine, are also known in the art. See, e.g. Melo e Silva et al., *Appl. Radiat. Isot.* 54:227-239 (2000) and U.S. Pat. No. 5,302,700, respectively.

The present invention is an improvement upon these synthetic methods. For labeling of nucleotides or nucleosides, generally the methods of Kassis et al. or Baranowska-Kortylewicz are followed, but an antioxidant is included after the radiohalogenation reaction so that the labeled product is protected from degradation during separation and storage steps. The resulting process allows the preparation of product having very high specific activity.

In a preferred embodiment of the process of the invention, related to labeling of a nucleoside or derivative thereof, a halogenated pyrimidine nucleoside, or derivative as noted above, is dissolved in solvent, preferably 1,4 dioxane, at a temperature of 40 to 60° C., preferably about 50° C. The solution is cooled to 20 to 30° C., preferably to room temperature and an alkylmetallic catalyst (preferably, but not limited to, bis(tributyltin)), and triphenylphosphine palladium are added. The solution is heated to 100 to 110° C., preferably to about 105° C. and maintained for 5 to 7 hours, preferably about 6 hours, under an inert atmosphere, preferably nitrogen or argon. The solvent is removed by evaporation, preferably under vacuum, and then the metallated (stannylated) product is obtained by flash chromatography on silica gel using a mobile phase comprising chloroform and methanol. The methanol is added as a linear gradient, to a final ratio of chloroform:methanol 4:1. Fractions are collected and the metallated (stannylated) pyrimidine is detected by thin layer chromatography. The product shows an Rf of 0.3 on thin layer chromatography on silica gel using a mobile phase of hexane:ether 1:1. The metallated pyrimidine is then reacted with Na$^{125}$I or other radiohalogen in a solution containing hydrogen peroxide or iodogen or other oxidant and a buffer, preferably a phosphate buffer. Iodogen tends to produce a good yield of high specific activity product. However it is not water soluble and so may contaminate the sample, thus rendering it unsuitable for medical use. Therefore, if iodogen is used in preparing a medical sample, care should be taken to as completely purify the product from the iodogen as possible. Hydrogen peroxide as an oxidant is water soluble and so can be easily removed during the downstream purification, but a lower yield of product is typically obtained. If hydrogen peroxide is used as the oxidant, it is typically used at a concentration of 0.1 to 0.5 mg/ml.

This oxidation step is generally described in U.S. Pat. No. 5,720,935. The pH should be acidic to neutral. That is, the pH should be about 7, preferably from 5 to 8, more preferably from 6 to 8 or 7 to 8 and is typically 7.4. Potassium salts of the halogen can also be used. The mixture is stirred for 1 to 5 minutes, preferably two to four minutes, more preferably about two minutes. Then an antioxidant, preferably vitamin C, is added to a concentration of 0.1 to 1 mg/ml, preferably from 0.3 to 1 mg/ml, more preferably about 0.5 mg/ml. The solution is then chromatographed over C$_{18}$ reverse phase matrix (e.g. Sep-Pak C18 cartridge) which has been previously washed with ethanol and then equilibrated with water. The column is then washed with water to remove unwanted material and the radiolabeled pyrimidine nucleoside (or other derivative thereof) is eluted with ethanol. Antioxidant, preferably vitamin C, can then be added to 0.1 to 1 mg/ml, preferably to 0.3 to 1 mg/ml, more preferably about 0.5 mg/ml, to the solution for final packaging and storage.

The product is packaged in any manner typical in the art, for example in a glass syringe bottle or screw-cap tube.

The amount of the antioxidant that is added is independent of the amount of labeled compound. However, if the solution of labeled compound contains more than 100 mCi, the antioxidant should be added at both the separation step and to the final product for packaging. On the other hand, if the solution of labeled compound contains less than 100 mCi, it is sufficient to add the antioxidant only during the separation step and then to package the final product in ethanol.

The final product is preferably packaged at a radioactive concentration of 100 to 200 mCi/ml.

Ethanol at a concentration of 95 to 100%, preferably at 100% can be used as the antioxidant in place of, or in combination with vitamin C to the extent that the radiolabeled compound is soluble in ethanol. Thus, when radiolabeled steroids are the intended product, ethanol can suitably be used at both the column purification and packaging steps. On the other hand, because antibodies and other proteins tend to denature upon contact with ethanol, vitamin C is the preferred antioxidant to be used when radio-labeled proteins are produced according to the invention.

EXAMPLE 1

Production of Radio-Labeled IUdR

Seven mmol of unlabeled iododeoxuridine (IudR, 2.5 g) was dissolved in 100 ml anhydrous dioxane at 50° C. The solution was then cooled to room temperature. 0.125 g of bis(triphenyl phosphine) palladium dichloride and 6 g (15 mmol) of hexabutylditin were added and the mixture was refluxed for 6 hours at 110° C. under argon. The solvent was removed under vacuum and the product was redissolved in chloroform methanol 4:1 and purified by chromatography over a silica gel column, eluting with a linear gradient of 0 to 20% methanol in chloroform. The product elutes in the range of 10 to 15% methanol. (The gradient of 0 to 20% methanol is run over 50 collection tubes; the product elutes in tubes 25 to 30.) The product is identified by ultraviolet fluorescence or iodine staining of a silica TLC plate developed with hexane:ether 1:1. The desired Bu$_3$SnUdR product was obtained as a pale yellow oil that exhibits a R$_f$ of 0.3.

Na$^{125}$I (200 mCi, produced by MDS Nordion) was added to a solution of 100 μg of Bu$_3$SnUdR in 250 ml of phosphate buffered saline, pH 7.4 containing 0.1 mg iodogen and the reaction was allowed to proceed for two minutes. Ascorbic acid was added to a concentration of 0.5 mg/ml and the solution was loaded onto a Sep-Pak™ C18 cartridge that was previously washed with 10 ml of ethanol, then washed three times, 10 mls each, with water. The cartridge was washed once with 1 ml water to remove free iodine and $^{125}$IUdr was eluted with 1 ml of ethanol, collecting the fractions containing radioactivity. 0.5 mg Ascorbic acid was added as a solution at 1 mg/ml in ethanol to the eluate. 180 mCi of $^{125}$IUdR at a specific activity of about 2000 Ci/mmol was obtained.

EXAMPLE 2

Labeling Proteins 132 microliters of 0.1 molecular potassium phosphate buffer at pH 8.2 was added to a vial containing 100 micrograms of polyclonal anti-TSH antibody and stirred for 10 seconds. 7 mCi of Na$^{125}$I was added to the solution. 40 microliters of chloramine T (CT) buffer solution at 1 mg/ml was added and stirred for 1 minute. 40 microliters of ascorbic acid buffer solution at 5 mg/ml was further added and stirred for 10 seconds. The iodinated polyclonal anti-TSH solution was then loaded into a G75 column (10 ml) and eluted with 0.01 M phosphate buffered saline at pH 7.4. 15 fractions in 13×100 MM test tubes were collected at the rate of 0.5 ml/tube at 2 minutes per tube (the product elutes in tubes 6-10). 1 ml of ascorbic acid buffer was added to a concentration of 1 mg/ml of 5% BSA phosphate saline buffer at pH 7.4. 4 mCi of $^{125}$I anti-TSH was obtained.

EXAMPLE 3

Labeling Steroids

Fifty microliters of DMF and 100 microliters of 0.2 M phosphate buffer at pH 7.4 was added to a vial containing 4 micrograms of Estradiol-6-CMO-Histamine Aliquot. 10 mCi of sodium I-125 was added to the solution and stirred for ~10 seconds. 50 microliters of chloramine T (CT) solution at 1 mg/ml was further added to the mixture and stirred for 3 minutes. 50 microliters of ascorbic acid buffer was then added at 5 mg/ml and injected into an HPLC, using a methanol/water (MeOH/H$_2$O) gradient. 0.5 ml fractions containing radioactivity were collected after 45 minutes. 10 ml of ethanol were added. 2.1 mCi of $^{125}$I Estradiol at a specific activity of about 2000 Ci/mmol was obtained.

What is claimed is:

1. A method for synthesizing a radiohalogenated pyrimidine comprising, in order:
   i) dissolving a halogenated pyrimidine in a first solvent 1,4 dioxane at a temperature of between 40 and 60° C. to form an initial solution, the pyrimidine being selected from a group consisting of nucleosides, nucleotides, ribonucleosides, deoxyribonucleosides, 2',3' dideoxynucleosides and 5' sugar-derivatized nucleosides and phosphonucleosides;
   ii) cooling the initial solution to a temperature of from 20 to 30° C. and adding bis(tributyltin) and triphenylphosphine palladium to the initial solution to produce a catalyzed solution;
   iii) heating the catalyzed solution under an inert atmosphere to a reaction temperature from 100 to 110° C. and for a reaction period of from 5 hours to 7 hours to produce an intermediate solution including a stannylated pyrimidine compound;
   iv) removing substantially all of the first solvent from the intermediate solution to obtain an intermediate composition, the intermediate composition including the stannylated pyrimidine compound;
   v) purifying the intermediate composition to produce a purified composition including the stannylated pyrimidine compound;
   vi) reacting the stannylated pyrimidine compound with a radiohalogen in a buffered reaction mixture at a pH from 5 to 8 to produce the radiohalogenated pyrimidine;
   vii) adding ascorbic acid to the reaction mixture; and
   viii) extracting the radiohalogenated pyrimidine from the reaction mixture to obtain a radiohalogenated pyrimidine for use as a diagnostic product.

2. The method for synthesizing a radiohalogenated pyrimidine according to claim 1, wherein:
   the pyrimidine is selected from a group consisting of nucleosides and nucleotides.

3. The method for synthesizing a radiohalogenated pyrimidine according to claim 1, wherein:
   the pyrimidine is deoxyuridine.

4. The method for synthesizing a radiohalogenated pyrimidine according to claim 1, wherein:
   the inert atmosphere is selected from a group consisting of argon, nitrogen and mixtures thereof; and
   the reaction mixture is buffered with a phosphate buffer and hydrogen peroxide.

5. The method for synthesizing a radiohalogenated pyrimidine according to claim 1, wherein:
   the halogenated pyrimidine is a 5-iododeoxypyrimidine;
   cooling the initial solution to 20 to 30° C. before adding the bis(tributyltin) and triphenylphosphine palladium to produce the catalyzed solution;
   the reaction temperature is from 100 to 110° C., the reaction period is about 6 hours and the inert atmosphere is an argon atmosphere;
   the first solvent is removed by rotary evaporation to obtain the intermediate composition;
   the reaction mixture includes a phosphate buffer and hydrogen peroxide, the reaction mixture being maintained for about 2 minutes to produce a radiohalogenated deoxypyrimidine;
   extracting the radiohalogenated deoxypyrimidine includes
   viii (a) binding the radiohalogenated deoxypyrimidine from the reaction mixture to a C$_{18}$ reversed-phase chromatography matrix;
   viii (b) washing the matrix with water;
   viii (c) eluting the radiohalogenated deoxypyrimidine with ethanol to obtain an eluate including the radiohalogenated deoxypyrimidine; and
   viii (d) adding a second antioxidant to the eluate to obtain the radiohalogenated product.

6. The method of claim 5, wherein
   the amount of the ascorbic acid added to the reaction mixture is from 0.1 to 1 mg/ml.

7. The method of claim 5, wherein
   the amount of the second antioxidant added to the eluate is from 0.1 to 1 mg/ml.

8. The method of claim 5, wherein
   the deoxypyrimidine is deoxyuridine.

9. The method for synthesizing a radiohalogenated pyrimidine according to claim 2, wherein:
   the pyrimidine is a nucleoside and wherein:
   extracting the radiohalogenated pyrimidine includes
   viii (a) applying the reaction mixture containing the radiohalogen labeled pyrimidine nucleoside to a chromatographic stationary phase whereby the radiohalogen labeled pyrimidine nucleoside is preferentially bound to the stationary phase;
   viii (b) washing the stationary phase having the radiohalogen labeled pyrimidine nucleoside bound thereto; and viii (c) eluting the radiohalogen labeled pyrimidine nucleoside from the stationary phase to obtain an eluate.

10. The method of claim 9, further comprising:
viii (d) adding a second antioxidant to the eluate.

11. The method of claim 10, wherein
the second antioxidant is ascorbic acid.

12. The method of claim 9, wherein
the concentration of the ascorbic acid is from 0.1 to 1 mg/ml.

13. The method of claim 11, wherein
the concentration of ascorbic acid is from 0.1 to 1 mg/ml.

14. The method of claim 9, wherein
the stationary phase is a $C_{18}$ reversed-phase matrix,
the column is washed with water in viii (b) and
the radiohalogen labeled pyrimidine nucleoside is eluted with ethanol in viii (c).

15. The method of claim 10, wherein
the stationary phase is a $C_{18}$ reversed-phase matrix,
the column is washed with water in viii (b) and
the radiohalogen labeled pyrimidine nucleoside is eluted with ethanol in viii (c).

16. The method of claim 9, wherein
the radiohalogen labeled pyrimidine nucleoside is $^{125}$I-labeled deoxyuridine.

17. The method of claim 10, wherein
the radiohalogen labeled pyrimidine nucleoside is $^{125}$I-labeled deoxyuridine.

18. The method of claim 14, wherein
the radiohalogen labeled pyrimidine nucleoside is $^{125}$I-labeled deoxyuridine.

19. The method of claim 15, wherein
the radiohalogen labeled pyrimidine nucleoside is $^{125}$I-labeled deoxyuridine.

20. The method for synthesizing a radiohalogenated pyrimidine according to claim 1, wherein
the radiohalogen is a radioisotope of an element selected from the group consisting of fluorine, chlorine, bromine and iodine.

21. The method for synthesizing a radiolabeled pyrimidine according to claim 1, wherein
purifying the intermediate composition includes flash chromatography over a silica gel matrix using a mobile phase consisting of an organic solvent.

22. The method of claim 21, wherein
the organic solvent includes a mixture of chloroform and methanol.

23. The method of claim 22, wherein
the chloroform and methanol are present in the mixture in a ratio of about 4:1.

* * * * *